United States Patent
Church et al.

(10) Patent No.: US 6,198,400 B1
(45) Date of Patent: Mar. 6, 2001

(54) PORTABLE GAS DETECTION AND/OR MONITORING APPARATUS FOR A HOSTILE ENVIRONMENT

(75) Inventors: Ross Trevor Church, Petrie; Brian Worth, Murrumba Downs, both of (AU)

(73) Assignee: App-Tek Pty Ltd., Kremzon Court (AU)

( * ) Notice: Subject to any disclaimer, the term of this patent is extended or adjusted under 35 U.S.C. 154(b) by 0 days.

(21) Appl. No.: 09/587,044

(22) Filed: Jun. 2, 2000

(51) Int. Cl.[7] .................................................. G08B 17/10
(52) U.S. Cl. ............................................ 340/632; 73/23.2
(58) Field of Search .................... 340/632, 633; 73/23.2; 435/807

(56) References Cited

U.S. PATENT DOCUMENTS

| | | | |
|---|---|---|---|
| 3,786,675 | * | 1/1974 | Delatorre et al. ............... 73/27 R |
| 5,214,412 | * | 5/1993 | Gaviak et al. ................... 340/632 |
| 5,305,231 | * | 4/1994 | Coppler et al. .................. 364/497 |

* cited by examiner

*Primary Examiner*—Jeffery A. Hofsass
*Assistant Examiner*—Son Tang
(74) *Attorney, Agent, or Firm*—Abelman, Frayne & Schwab

(57) ABSTRACT

Portable gas detection and/or monitoring apparatus including a case having a substantially cylindrical wall and two opposite end caps sealably connected to the cylindrical wall, at least one of the end caps being removable from the cylindrical wall, and at least a portion of the cylindrical wall being transparent. A gas detection and/or monitoring unit is mounted in the case and includes gas sensing means in sealed fluid communication with the ambient atmosphere outside the case. Data processing means is operatively connected to the gas sensing means, and data storage means and information display means is operatively connected to the data processing means. Calibrating means is operatively connected to the data processing means for calibration thereof to a predetermined gas concentration measured by the gas sensing means, the calibrating means including externally operable switching means for selectively connecting the data processing means to the data storage means to allow transfer of data from said data storage means to said data processing means. Communication means is operatively connected to the data processing means or the data storage means for communicating data to the data processing means or the data storage means to an external destination and/or vice versa. A power supply is mounted in the case and operatively connected to the gas detection and/or monitoring unit and/or the gas sensing means.

14 Claims, 4 Drawing Sheets

PORTABLE GAS DETECTION AND/OR MONITORING APPARATUS FOR A HOSTILE ENVIRONMENT

This invention relates to portable gas detection and/or monitoring apparatus. The invention has been developed primarily for use with data logging capability for logging data relating to the presence or concentration of a gas or gases, and reference is made herein to such application. However, it will be appreciated that the invention is not limited to this field of use and may be used in general gas detection and/or monitoring applications.

Although gas detectors and monitors have been used for many years, they have often been restricted to non-hostile or non-corrosive environments due to the effect of corrosive gases on electrical and/or electronic components. Sealed units have been provided, but have been difficult and costly to service and maintain, particularly in relation to preventing ingress of gas into the apparatus.

The present invention is aimed at providing portable gas detection and/or monitoring apparatus which alleviates one or more of the abovementioned problems, although other aims and advantages may hereinafter become apparent from the following description.

With the foregoing in view this invention in one aspect resides broadly in portable gas detection and/or monitoring apparatus including:

a case having a substantially cylindrical wall and two opposite end caps sealably connected to said cylindrical wall, at least one of said end caps being removable from said cylindrical wall, and at least a portion of cylindrical wall being transparent;

a gas detection and/or monitoring unit mounted in said case, said gas detection and/or monitoring unit including
gas sensing means in sealed fluid communication with the ambient atmosphere outside said case,
data processing means operatively connected to said gas sensing means,
data storage means and information display means operatively connected to said data processing means,
calibrating means operatively connected to said data processing means for calibrating said data processing means to a predetermined gas concentration measured by said gas sensing means, said calibrating means including externally operable switching means for selectively connecting said data processing means to said data storage means to allow transfer of data from said data storage means to said data processing means, and
communication means operatively connected to said data processing means or said data storage means for communicating data to said data processing means or said data storage means to an external destination and/or vice versa; and a power supply mounted in said case and operatively connected to said gas detection and/or monitoring unit and/or said gas sensing means.

Preferably, said gas sensing means is mounted to an end cap and is in sealed fluid communication via a passage provided in said end cap.

Preferably, said communication means is wireless and in a preferred form uses electro-magnetic radiation, preferably in the infra-red band, thus allowing a communication link to be established without forming an opening in said case.

Preferably, the length and diameter of the cylindrical wall approximates that of well known Coca-Cola cans and thus is easy to handle by persons used to handling Coca-Cola or other beverages in similar sized cans. Thus, it will be appreciated that the length and diameter of the cylindrical wall is selected to be easy to handle by an adult human hand.

It is also preferred that at least one of the end caps include support means whereby the apparatus may be supported in a hostile environment. In a preferred form, the support means is in the form of an inverted U-shaped bolt or handle fixed to one end cap (the "upper" end cap) with the open ends of the "U" being closed by their attachment to the end cap. The size of the U-shaped handle is selected to permit the apparatus to be suspended from a hook, shackle, eyebolt, chain or the like.

Preferably, the information display means is spaced from said end walls and said cylindrical wall thus being protected to a large extent from physical damage.

Preferably, the apparatus also includes an audible alarm which is operatively connected to said data processor and set to sound in response to the concentration of gas being measured reaching a predetermined level. In a preferred form the audible alarm is mounted in one end cap opening on one side to a passage through the end cap and encased on all other sides in a resin with a cable or other suitable electrical conduit extending from the resin for connection to said data processor. Advantageously, this arrangement prevents the ingress of moisture or gases into the case via the audible alarm.

It is also preferred that the calibration means includes remotely operable electrical contact means operable to close one or more electrical connections remotely, such as by magnetism. Preferably, there are separate electrical contacts for setting a null and a span whereby the gas sensing means may be calibrated to a zero or null value and a span without opening the case by closing the respective electrical contacts in a predetermined sequence.

The apparatus preferably includes an internal power supply, such as an electrical cell or battery. In a preferred embodiment, the power supply is induction chargeable to avoid the requirement for opening the case for replacement and/or recharging of the cells or batteries.

Preferably, the externally operable switching means includes a momentary contact switch, and the data processing means is programmed to selectively connect the data processing means to the data storage means upon operating the switch to close according to a predetermined sequence and/or timing.

In order that the invention may be more readily understood and put into practical effect, reference will now be made to the accompanying drawings which illustrate one or more preferred embodiments of the invention, and wherein.

Figure 1:
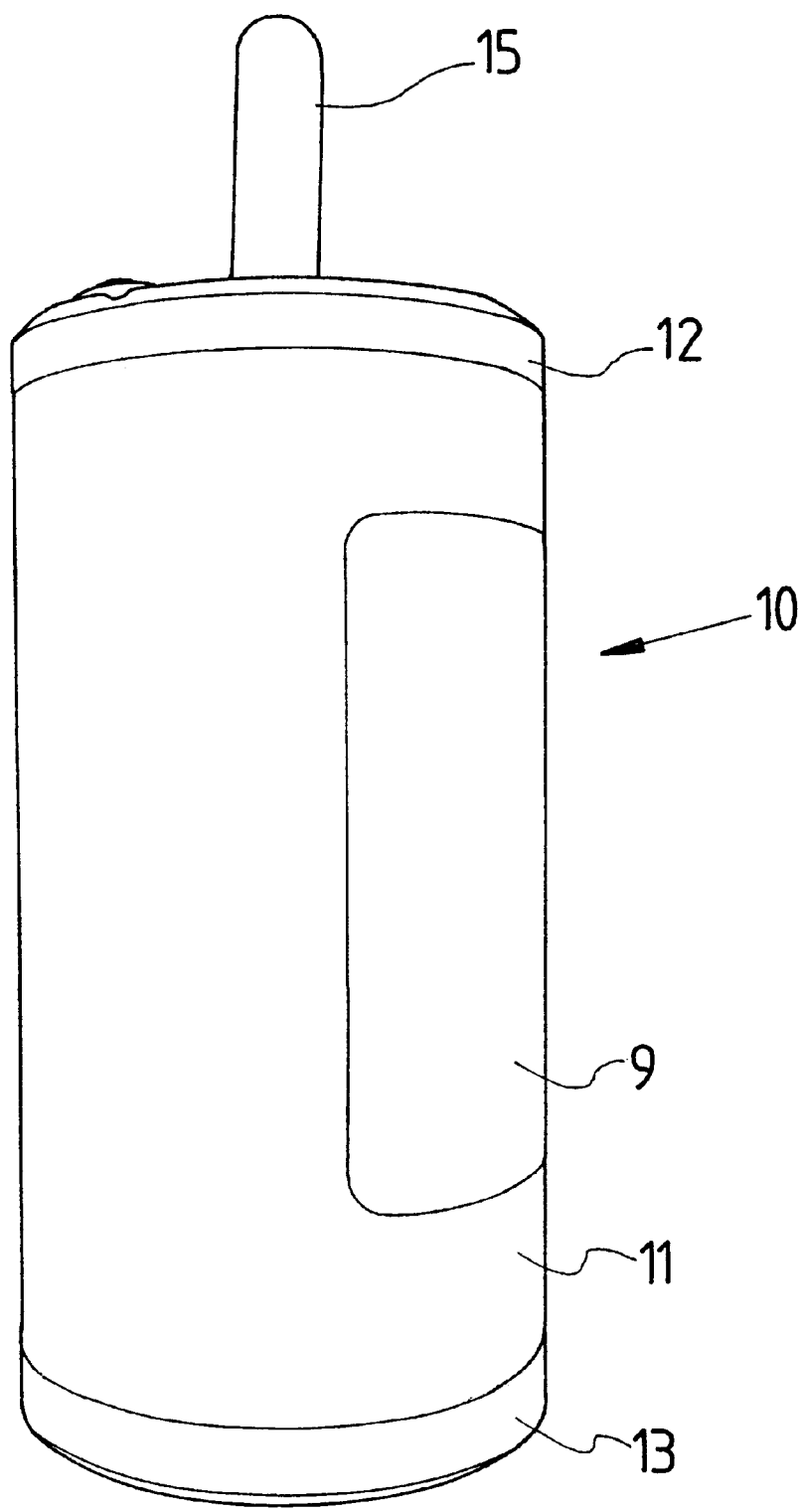
FIG. 1 is a pictorial representation of a portable gas detection and/or monitoring apparatus according to the invention.
Figure 2:
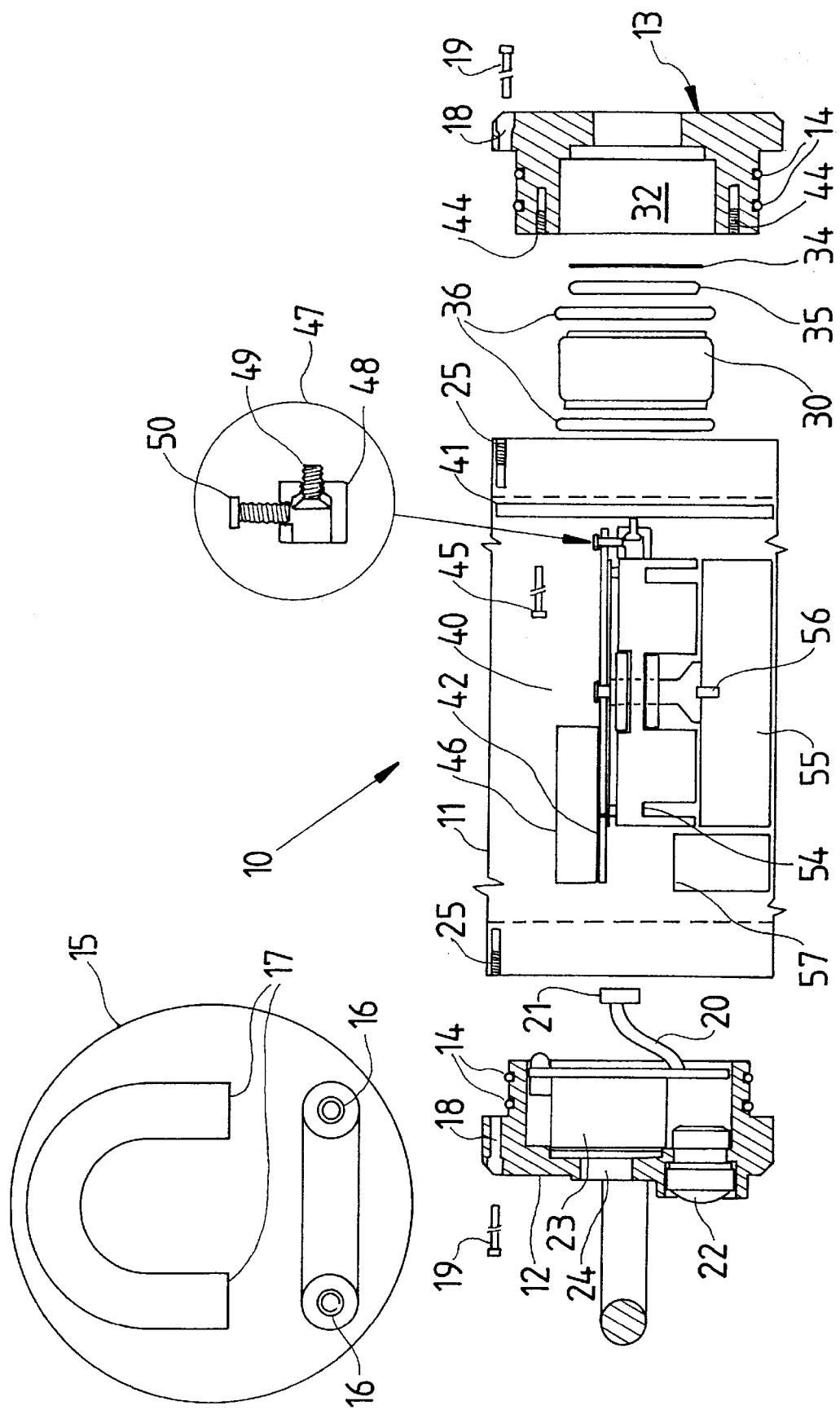
FIG. 2 is diagrammatic part section exploded view of the portable case and/or monitoring apparatus of FIG. 1.

The portable gas detection and/or monitoring apparatus 10 shown in FIG. 1 includes a case having a cylindrical wall 11 with an upper end cap 12 and lower end cap 13 fixed to the wall. The end caps sealingly enclose the space within the case for accommodating a gas detection and/or monitoring unit 40, although as described hereinafter, some of the gas detection monitoring unit is mounted to one or both of the end caps. Each end cap is provided with three counterbored screw holes 18 (one of which is shown in FIG. 2) spaced equi-angularly around the periphery of the end caps and through which a box head screw 19 may be passed to engage with a corresponding threaded aperture 18 extending axially inward from the respective end faces of the cylindrical wall. Two O-rings 14 are provided in respective grooves in each end cap for sealing engagement with the inner cylindrical face of the cylindrical wall to seal the enclosed space described above when the end caps are placed in their respective positions to form the case. Each end cap has a shoulder which bears against a respective end face of the cylindrical wall into which the threaded apertures 25 are provided.

An inverted U-shaped handle shown in elevation and bottom plan view in the detail 15 is secured to the outer and upper face of the upper end cap by inserting a screw (not shown) into a corresponding threaded aperture 16 in the two distal faces 17 of the handle 15.

A momentary contact switch 22 is sealed into a corresponding aperture in the upper end cap between the centre and one side (the "rear" side) of the cap as shown. Additionally, a speaker 23 is embedded in a resin in a corresponding internal recess in the upper end cap in operative alignment with a centrally located speaker aperture 24. The embedding of the speaker seals against ingress of moisture, but also permits the operation of the speaker when activated by the remainder of the electrical circuitry of the apparatus. The speaker and switch are electrically connected by a lead 20 to an electrical terminal 21 which provides for electrical connection of the switch and speaker to the remainder of the electrical circuitry of the gas-detection and/or monitoring unit 40.

A gas sensor 30 is sealed into an internal recess 32 in the lower end cap, and a gas permeable membrane 34 is used to substantially prevent the ingress of moisture into the recess, the membrane being sealed in place by an O-ring 35, and the sensor being sealed into the recess 32 by two O-rings 36, one at each end of the gas sensor.

The gas detection and/or monitoring unit 40 is sealed within the cylindrical wall 11 and the end caps 12 and 13. The majority of the electronic components for the unit 40 are mounted to a circular printed circuit board 41 and a rectangular printed circuit board 42. The circular printed circuit board is mounted to the lower end cap by way of four screws, one of which is shown at 45, and each being inserted into a respective threaded aperture 44 so that the circular printed circuit board is supported normal to the axis of the case. A mounting assembly 47 is used to mount the rectangular printed circuit board to the circular printed circuit board substantially at right angles, the mounting assembly including a bracket 48 which is mounted to the circular printed circuit board by way of a countersunk screw 49 and the rectangular printed circuit board being mounted to the bracket by way of a box head screw 50. This arrangement provides that the rectangular printed circuit board is supported in a position at or close to a diametral plane across the cylindrical space within the case, but extending only part-way across with even spacing on each side whereby the rectangular circuit board and the electronic componentry mounted thereon is spaced inwardly from the cylindrical wall to provide protection from inward deformation of the cylindrical wall, for example, due to bumping or crushing.

A dry cell battery pack 54 is mounted to the rear of the rectangular printed circuit board by way of a mounting screw 56, and a retainer in the form of a foam block shaped to complement the shape of the dry-cell battery pack and the internal curved surface of the cylindrical wall is provided between the dry cell battery pack and the rear portion of the space behind the battery pack. Additionally, a moisture absorbent pack 57 is located between the battery pack and the upper end cap.

Figure 3:
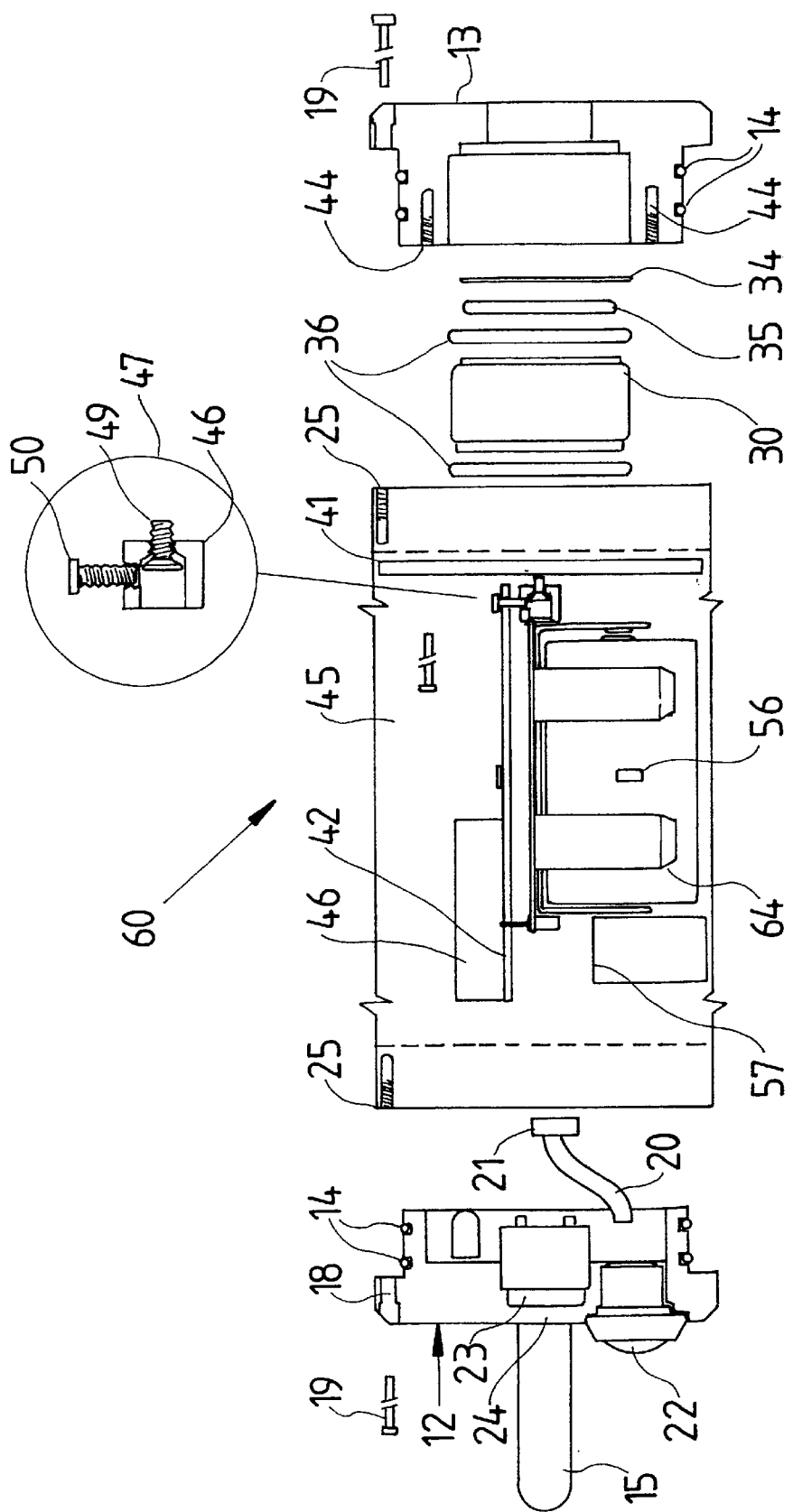
FIG. 3 is a diagrammatic part section exploded view of the portable gas detection and/or monitoring apparatus of FIG. 1 with an alternative form of upper end cap and power supply.
Figure 4:
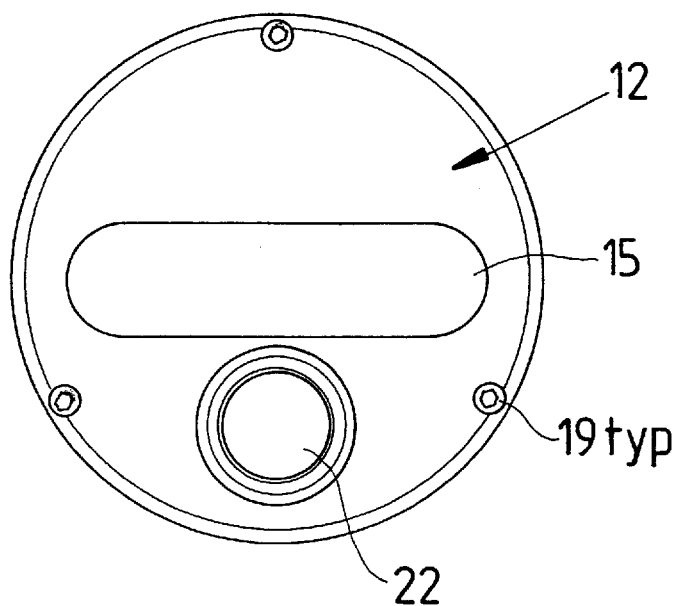
FIG. 4 is a plan view of the top of the portable gas detection and/or monitoring apparatus of FIG. 1.

Referring to FIGS. 3 and 4, a slightly different portable gas detection and/or monitoring apparatus 60 is shown in which the cylindrical wall, gas detection and/or monitoring unit, gas sensor, speaker, handle, momentary contact switch and such-like are of the same form as provided in the portable gas detection and/or monitoring apparatus 10 described in respect of FIGS. 1 and 2. Accordingly, like parts are given the same reference numerals as those of FIGS. 1 and 2. However, a modified upper end cap 61 is provided which has a substantially flat upper face, and the dry cell battery pack 54 of FIG. 2 is replaced by a lithium cell battery pack 64 in FIG. 3 which does not require the retainer 55.

Figure 5:
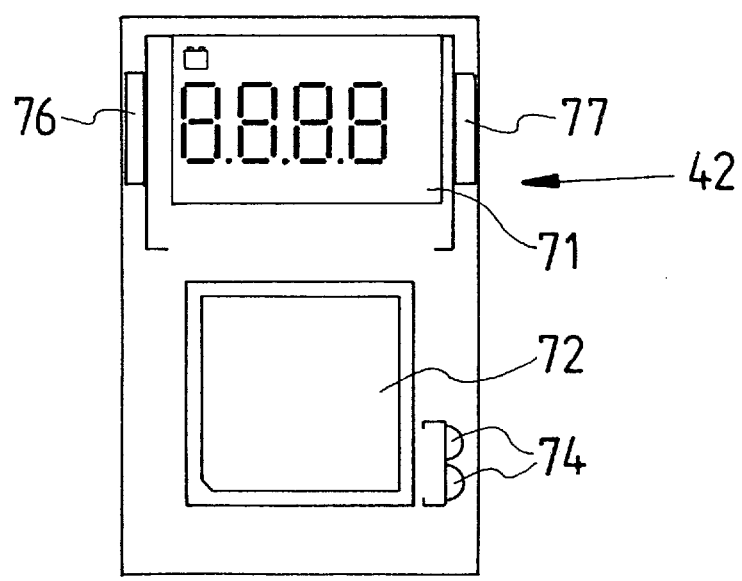
FIG. 5 is a front view of a rectangular printed circuit board for the portable gas detection and/or monitoring apparatus of FIG. 1.

Referring to FIG. 5, the rectangular printed circuit board 42 includes a display 71 and an integrated circuit chip 72 mounted to the upper and lower portions of the rectangular printed circuit board respectively. The display and the rectangular printed circuit board are shown as seen through a window provided in the cylindrical wall of the case as shown in FIG. 1, with the window being given reference numeral 9. To the right of the integrated circuit chip is provided an infra red sensor assembly 74, and to the left and right of the display is provided a null switch 76 and a span switch 77 respectively. The null and span switches are magnetically activated reed switches. The window is provided by forming the cylindrical wall from a clear light transmissible material and covering the external surface with a covering or coating with the window being of sufficient size such that corrosion of the circuitry may be observed therethrough.

The portable gas detection and/or monitoring apparatus of the present invention may be assembled by screwing the assembled printed circuit boards together and then screwing the round printed circuit board to the lower end cap. The lower end cap is then installed on the end of the cylindrical wall by inserting the working parts into the hollow cylinder and screwing the end cap in place. The upper end cap is assembled by providing an upper end cap circuit board having the switch, lead and speaker to the upper end cap circuit board mounted thereto and which is in turn mounted to the inner side of the upper end cap. The lead is then, and then electrically connected to the rectangular printed circuit board and the upper end cap screwed to the upper end of the cylindrical wall to complete the assembly of the case and the sensor circuitry therein. If desired, a light emitting diode may be provided in parallel to the speaker and mounted to the upper end case circuit board. As an alternative to screwing the upper end cap circuit board to the upper end cap, the speaker and the light emitting diode may be potted in a resin in the upper end cap to seal against moisture and/or dust from ingress past the light emitting diode and the speaker.

The space within the case is preferably at least partly pressurised, the screws in the end caps being selected to provide sufficient stability under the axial load produced by the pressure. This pressurisation, is designed to further inhibit the ingress of moisture and dust, and it is believed that sufficient pressurisation will be achieved by the sliding of the O-rings axially inward and containing the air entrapped in the cylindrical space during the assembly of the apparatus.

In use, the portable gas detection and/or monitoring apparatus of the present invention may be installed in an environment in which a particular gas is to be detected and/or monitored by securing the apparatus to an appropriate location by way of, for example, a hook or shackle to the U-shaped handle and suspending the apparatus in the environment. The integrated circuit chip may be programmed to operate the unit as described hereinafter, but it will be appreciated that this is a specific example and other modes of operation may be programmed.

The portable gas detection and/or monitoring apparatus may be switched on by pressing and holding the momentary contacts which in the "ON" position for three or more seconds and then releasing. The display will show (consecutively) a "test screen" (in which the four numerals "8.8.8.8" will be shown, followed by the installed firmware version, followed by a "statistics" indication (StAt) which displays in order: "Cloc" (Clock), time of day, temperature, "bAtt" (Battery), Battery voltage, "LOG", percentage of logging memory used, and an indication of the status which has been selected at the time the apparatus is switched on, the logging interval, and the logging time unit. The display will then revert to display the instantaneous gas readings in parts per million (ppm) on the "test screen" numerals (8.8.8.8).

Different modes of operation of the gas detection and/or monitoring apparatus can be selected by pressing and holding down the momentary contact switch 22 until the appropriate status indication on the display is activated, and then releasing the momentary contact switch. For example, the current statistics can be displayed on the display be pressing and holding the momentary contact switch until the "StAt" indicator is displayed and the display back light may be activated every time the momentary contact switch is closed to make the display readable in poor lighting conditions. The logging function may be commenced and stopped by holding the contact switch closed until the "StAt" indication is activated, but released when the "LOG" indicator is shown on the display. An infra red communication link mode may be entered and exited by pressing and holding the momentary contacts which until the "IrdA" mode is indicated on the display and then released. The apparatus may be programmed so that the infra red communication link mode can only be entered when logging is stopped. The apparatus may also be turned off by pressing and holding the momentary contact switch and waiting for the display to cycle through its screens until "OFF" is displayed, and then keeping the button depressed for three seconds. The timing for the operation of the gas detection and/or monitoring unit, as well as the operation of the alarms, may also be programmed into the memory of the gas detection and/or monitoring unit.

It will be appreciated that different gas sensors may be used, and may be able, for example, to detect and/or monitor the presence above a particular concentration, or the concentration of hydrogen sulfide, carbon monoxide, sulfur dioxide, nitrous or nitric oxide, cyanide, hydrogen chloride gas, ammonia, ozone, chlorine, hydrogen gas, ethylene oxide, ethane, methane, or carbon dioxide. Adjustments may be made for the presence of interfering gases in accordance with known interference tables.

The null and span switches may be used to calibrate the gas detection and/or monitoring unit, when the unit has been activated into its calibration mode by use of the momentary contact switch as described above, and data logged into the memory of the portable gas detection/measuring apparatus may be downloaded by way of the infra red link to an external source, such as a personal computer, for analysis and or reporting.

Although the invention has been described with reference to one or more specific examples, it will be appreciated by those skilled in the art that the invention may be embodied in many other forms as defined by the following claims.

What is claimed is:

1. Portable gas detection and/or monitoring apparatus including:
   a case having a substantially cylindrical wall and two opposite end caps sealably connected to said cylindrical wall, at least one of said end caps being removable from said cylindrical wall, and at least a portion of said cylindrical wall being transparent;
   a gas detection and/or monitoring unit mounted in said case, said gas detection and/or monitoring unit including
   gas sensing means in sealed fluid communication with the ambient atmosphere outside said case,
   data processing means operatively connected to said gas sensing means,
   data storage means and information display means operatively connected to said data processing means,
   calibrating means operatively connected to said data processing means for calibrating said data processing means to a predetermined gas concentration measured by said gas sensing means, said calibrating means including externally operable switching means for selectively connecting said data processing means to said data storage means to allow transfer of data from said data storage means to said data processing means, and
   communication means operatively connected to said data processing means or said data storage means for communicating data to said data processing means or said data storage means to an external destination and/or vice versa; and
   a power supply mounted in said case and operatively connected to said gas detection and/or monitoring unit and/or said gas sensing means.

2. Portable gas detection and/or monitoring apparatus according to claim 1, wherein said gas sensing means is mounted to an end cap and is in sealed fluid communication via a passage provided in said end cap.

3. Portable gas detection and/or monitoring apparatus according to claim 1, wherein said communication means is wireless communication means in an infra-red band.

4. Portable gas detection and/or monitoring apparatus according to claim 1, wherein said information display means is spaced from said end walls and said cylindrical wall.

5. Portable gas detection and/or monitoring apparatus according to claim 1, and including an audible alarm operatively connected to said data processor and set to sound in response to a concentration of gas being measured reaching a predetermined level.

6. Portable gas detection and/or monitoring apparatus according to claim 5, wherein said audible alarm is mounted in one end cap opening on one side to a passage through said end cap and encased on all other sides in a resin with an electrical conduit extending from said resin for connection to said data processor.

7. Portable gas detection and/or monitoring apparatus according to claim 1, wherein the length and diameter of the cylindrical wall is selected to be easy to handle by an adult human hand.

8. Portable gas detection and/or monitoring apparatus according to claim 1, wherein at least one of said end caps includes support means whereby said apparatus may be supported in a hostile environment.

9. Portable gas detection and/or monitoring apparatus according to claim 8, wherein said support means is in the form of an inverted U-shaped bolt or handle fixed to one end cap (the "upper" end cap) with the open ends of the "U" being closed by their attachment to said upper end cap.

10. Portable gas detection and/or monitoring apparatus according to claim 1, wherein said information display means is spaced from said end walls and said cylindrical wall a distance sufficient to protect said information display means from physical damage.

11. Portable gas detection and/or monitoring apparatus according to claim 1, wherein said calibration means includes remotely operable electrical contact means operable to close one or more electrical connections remotely.

12. Portable gas detection and/or monitoring apparatus according to claim 11, wherein said electrical contact means is operable by magnetism.

13. Portable gas detection and/or monitoring apparatus according to claim 11, wherein said electrical contact means includes separate electrical contacts for setting a null and a span whereby said gas sensing means may be calibrated to a zero or null value and a span without opening said case by closing the respective said electrical contacts in a predetermined sequence.

14. Portable gas detection and/or monitoring apparatus according to claim 1, wherein said power supply includes an induction chargeable secondary cell or battery.

* * * * *